United States Patent [19]

Sahota

[11] Patent Number: 5,019,042
[45] Date of Patent: May 28, 1991

[54] BALLOON CATHETERS

[76] Inventor: Harvinder Sahota, 3861 Wisteria, Seal Beach, Calif. 90740

[21] Appl. No.: 510,470

[22] Filed: Apr. 18, 1990

Related U.S. Application Data

[62] Division of Ser. No. 276,375, Nov. 23, 1988, Pat. No. 4,983,167.

[51] Int. Cl.$^5$ ............................................. A61M 29/00
[52] U.S. Cl. ...................................... 604/101; 604/96; 606/194
[58] Field of Search ......................... 604/101, 96, 95; 606/192, 194

[56]  References Cited

U.S. PATENT DOCUMENTS

| | | | |
|---|---|---|---|
| 3,045,677 | 7/1962 | Wallace | 604/192 |
| 4,040,413 | 8/1977 | Ohshiro . | |
| 4,233,983 | 11/1980 | Rocco . | |
| 4,423,725 | 1/1984 | Baran et al. . | |
| 4,527,549 | 7/1985 | Gabbay | 604/192 |
| 4,546,759 | 10/1985 | Solar | 604/101 |
| 4,581,017 | 4/1986 | Sahota . | |
| 4,763,654 | 8/1988 | Jang | 604/195 |

OTHER PUBLICATIONS

USCI Gruntzig TM Femoral, Iliac and Gruntzig Dilaca TM Renal Dilatation Catheters, C. R. Bard, Inc. 1980.
Gruntzig Dilaca ® Coronary Balloon Dilatation Catheters, ©C. R. Bard, Inc. 1982 USCI ® Probing Catheter.

Primary Examiner—Stephen C. Pellegrino
Assistant Examiner—Ralph A. Leiois
Attorney, Agent, or Firm—Knobbe, Martens, Olson & Bear

[57]  ABSTRACT

Dilatation catheters for use in administering treatments to relieve stenotic regions within a body lumen are described. In one aspect of the invention, a two wire catheter system, of minimal diameter for treating distal arteries is disclosed. In addition, a number of various dilatation balloon configurations, for treating stenotic areas which are present in tortuous vessels, as well as hardened, or calcified stenotic portions are also described. Finally, a catheter system which provides a path for conducting blood past the stenosis and inflated dilatation balloon is discussed.

1 Claim, 4 Drawing Sheets

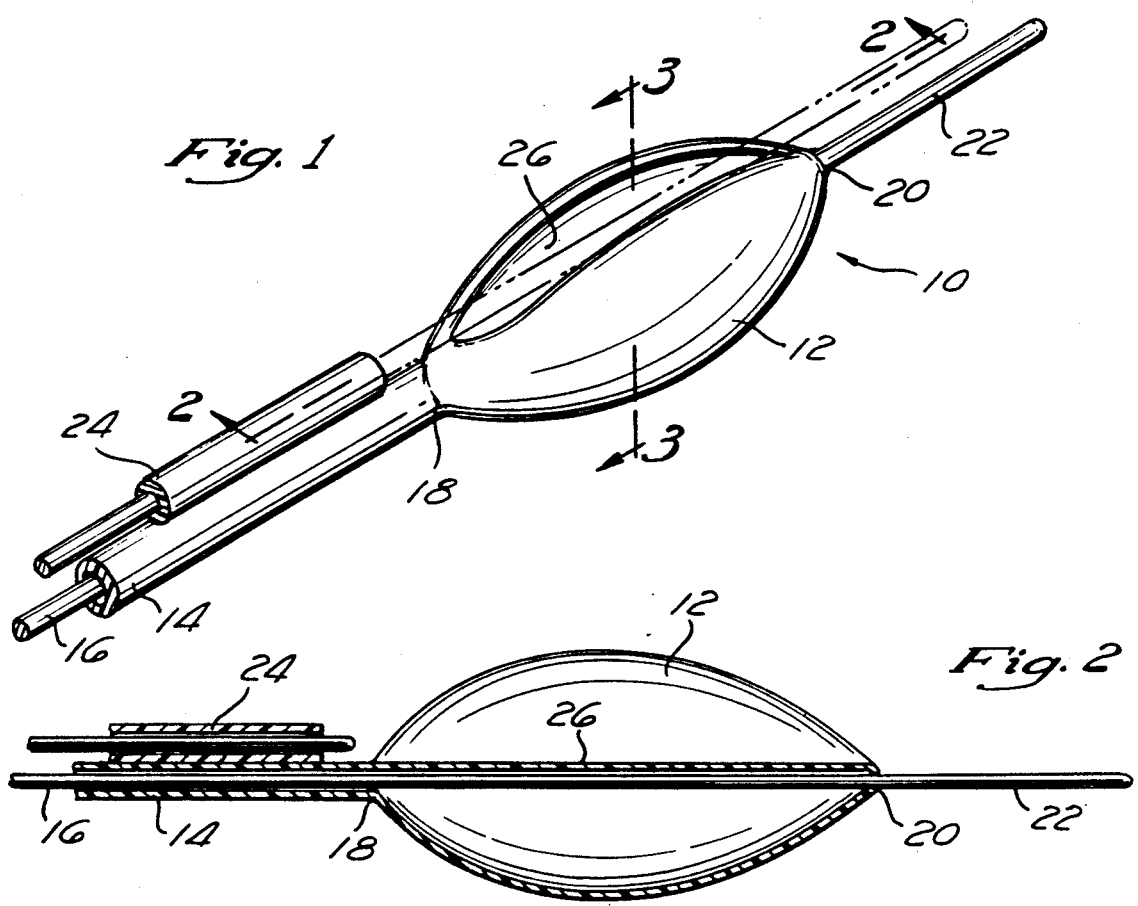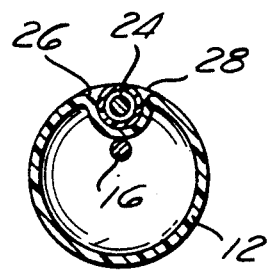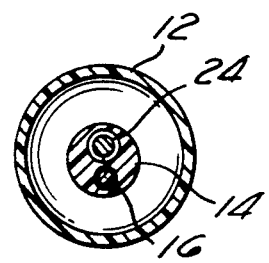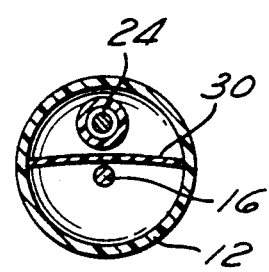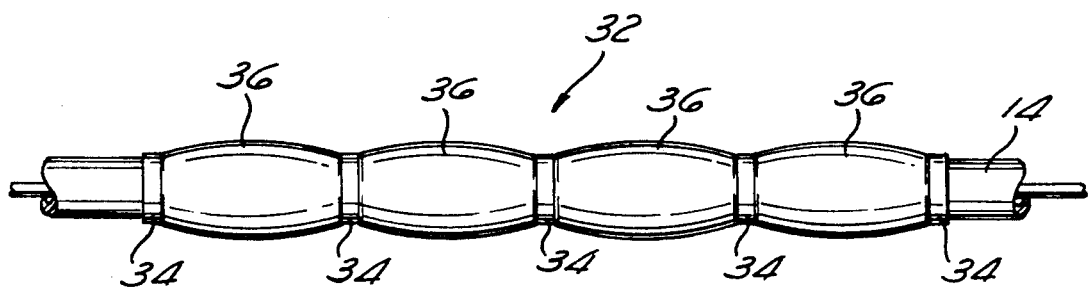

BALLOON CATHETERS

This application is a division, of application Ser. No. 276,375, filed 11/23/88 now U.S. Pat. No. 4,983,167.

BACKGROUND OF THE INVENTION

The present invention relates generally to the field of catheters. More specifically, the present invention relates to dilatation catheters for use in administering treatments to relieve a stenotic region or to widen a constricted blood flow or tubular passage, such as the coronary artery, as well as other vessels.

Percutaneous transluminal coronary angioplasty (PTCA), a procedure for treating a patient having a stenosis or constricted blood region in a coronary artery, has become a widely accepted therapeutic alternative to coronary arterial bypass surgery for many patients. PTCA increases the lumen by radial expansion. The main advantage of PTCA rests in the avoidance of the immediate post-operative discomforts associated with coronary bypass surgery, and certainly in the reduction of morbidity by use of this procedure.

The benefits of PTCA are restricted to lesions accessible to the balloon dilatation catheter. With standard systems, certain lesions are inaccessible due to variations in the patient's anatomy and vasculature. Further, seducing side branches, tortuous vessels, and the more distal arteries have presented serious difficulties in the PTCA procedure because, due to its cross-sectional area, the balloon could not reach the stenotic region.

Performing a coronary angioplasty involves the difficulty of inserting a balloon catheter into the desired coronary artery. Most balloon catheters are too flexible for direct insertion into the patient's coronary artery. Accordingly, the standard angioplasty process begins with the insertion of a guiding catheter, or sleeve into the obstructed vessel, under local anesthesia. To facilitate the introduction of the guiding catheter, and to avoid damage to the body lumen at the puncture site, a guide wire may be useful in the insertion of the guiding catheter. The guiding catheter is designed to provide a conduit through which a balloon catheter is passed. Preferably, the tip of the guiding catheter is not tapered so as to permit the unimpeded passage of the balloon catheter therethrough.

When considering angioplasty as a method of treating stenotic regions, the morphology of the lesion is critical in determining whether the balloon catheter can be safely passed beyond the stenosis, and whether the vessel will adequately dilate. If the stenosis is comprised primarily of fatty deposits, for example, it is often times possible to compress the stenosis radially outwardly, against the adjacent vessel wall, so as to increase the cross-sectional area of the vessel, and provide adequate perfusion through the vessel. If, however, the artery is hard, or the stenosis has calcified, a standard balloon might burst when inflated. Further, tortuous hardened arteries may be dissected if inflated with such a dilatation balloon.

The lesion may be approached with a guide wire by advancing the catheter and guide wire as a unit, or by advancing the guide wire first. Steering the tip of the wire is done by the surgeon or by an assistant. If the tip is moving in an undesired direction, then slight withdrawal and rotation of tip will point it in the correct way. Once the wire is positioned, the balloon catheter may be advanced over it until it crosses the lesion while the surgeon pulls back on the guide wire to maintain the tip in a fixed position in the distal coronary. If resistance is encountered at the lesion, gentle pressure on the balloon catheter will often cause it to cross. If, however, the lesion is too tight or hard and the balloon tip still will not cross, a new, low profile catheter must be selected. In this instance, the safety of the movable guide wire system must be sacrificed.

Ordinarily, a cardiologist, administering an angioplasty treatment, does not know how much pressure to apply to the balloon to achieve satisfactory results. Since the balloon is non-distensible, it can be inflated only to the constructed size of the balloon. Further attempts to force fluid into the balloon will result in increased pressure, but no significant increase in diameter. However, excessive pressure in the balloon may dissect the artery, which may cause serious damage to the patient's heart.

Therefore, the cardiologist positions the balloon in the artery, expands the balloon, and then allows the balloon to depressurize to permit measurement of blood flow across the stenosis. If the blood flow rate is not acceptable, the cardiologist must repeat the angioplasty treatment, often times necessitating the insertion of multiple catheters, of progressively larger diameters, to gradually increase the lumen of the artery until the obstruction is either alleviated, or until the cardiologist determines that angioplasty will be unable to restore the blood flow rate to an acceptable value.

When the angioplasty procedure requires the insertion and withdrawal of a great many balloon catheters, the risk of damage to the lining of the blood vessel is substantially increased. All blood vessels have a lining of very flattened cells, known as endothelial cells, the integrity of which is essential to normal blood flow. Damage or injury to the endothelial layer promotes the adherence of blood cells passing through the vessel at the point of injury, and may form further obstructions within the artery or vessel.

SUMMARY OF THE INVENTION

The dilatation catheters of the present invention overcome many of the difficulties associated with ordinary prior art dilatation catheters. In one aspect of the invention, a two wire system, of minimal diameter is disclosed. In this embodiment, the dilatation balloon is secured directly to an advance wire and a second movable wire is provided. Advantageously, following the inflation and deflation of the dilatation balloon, the catheter is withdrawn across the lesion while the second, movable wire is advanced, so as to keep it far distal to the dilated segment. Significantly, if the results are unsatisfactory, or if dissection or other filling defects obscure the lesion, the same dilatation balloon, or a different size or type of dilatation balloon can be quickly and safely passed across the stenosis over the second wire which has been left in place. In addition to providing distal access to the dilated segment, the movable wire gives strength and support along the length of the catheter during insertion thereof, while maintaining the smallest possible profile at the distal end of the catheter to facilitate the ease of insertion past the stenotic region. The added strength and support of the catheter is helpful in manipulating the catheter through the desired vessels.

In another aspect of the present invention, a multi-lobed balloon is described. In some arteries, for example, the left anterior descending artery, there are many sharp bends and curves. Seducing such tortuous vessels can prove quite difficult using standard, single lobed dilatation balloons. The multi-lobed dilatation balloon of the present invention advantageously readily deforms to assume the shape of the artery, both during insertion and inflation thereof. Thus, acute bends may be dilated without substantial risk of straightening out the artery, which can lead to dissection.

In a third aspect of the present invention, a dilatation catheter, designed to be used in connection with a conventional guide wire type system, having perfusion ports is described. In this embodiment, a plurality of perfusion ports are provided for permitting blood to enter into a perfusion lumen for passage therethrough past the dilatation balloon and stenosis, and exit back into the artery through a second plurality of perfusion ports so as to maintain continuity of blood flow within the blood vessel.

In yet another aspect of the present invention, the dilatation balloon is comprised of several layers of gradually increasing balloon sizes, so as to give the balloon increased strength and elasticity. This embodiment is especially useful in dilating hard or calcified lesions which require excessive pressures to adequately dilate the vessel, without major risk of bursting the balloon. The balloons are expanded from the innermost balloon outward, until the vessel has been dilated to a level at which sufficient blood flow is allowed to pass the stenotic region.

Further objects, features and other advantages of the present invention will become apparent from the ensuing detailed description, when considered together with the appended drawings.

BRIEF DESCRIPTION OF THE DRAWINGS

FIG. 1 is a perspective view of a dilatation catheter;

FIG. 2 is a cross-sectional view, taken along line 2—2 of FIG. 1, showing the positioning of a second wire with respect to the dilatation balloon, prior to insertion into a body lumen;

FIG. 3 is a cross-sectional view, taken along line 3—3 of FIG. 1, illustrating one possible arrangement of the second movable wire;

FIG. 3a is a cross-sectional view of an alternative method of securing the second wire to the balloon dilatation catheter of FIG. 1;

FIG. 3b is a cross-sectional view of a second alternative method of securing the second wire to the balloon dilatation catheter of FIG. 1;

FIG. 4 is a perspective view of a multi-lobed dilatation balloon;

DETAILED DESCRIPTION OF THE PREFERRED EMBODIMENT

Figure 5:
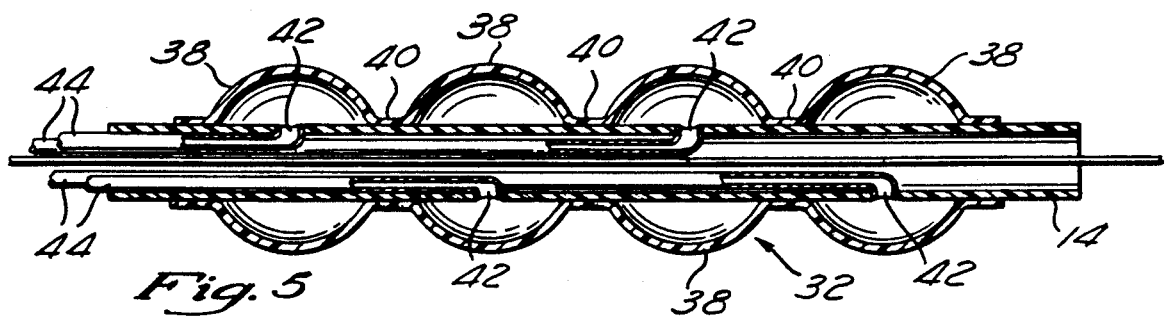
FIG. 5 is a cross-sectional view of the multi-lobed dilatation balloon of FIG. 4, illustrating separate inflation lumen and ports for each lobe of the balloon.

Referring now to the drawings in detail, wherein like reference numerals designate like elements throughout the several views thereof, there is shown generally at 10, in FIGS. 1 and 2, a dilatation catheter embodying the present invention in a preferred form. The catheter 10 comprises a dilatation balloon 12, having a distal end 20 which is fastened around an axially elongate wire 16. By attaching the dilatation balloon 12 directly on the wire 16, the catheter 10 has an exceedingly small cross-sectional area, especially designed for insertion into the most distal arteries which are much narrower than the main coronary artery. Preferably, the dilatation balloon 12 is attached to the wire 16 only at the distal end 20, leaving the wire 16 free to move within the shaft 14. Preferably, the wire 16 extends the length of the catheter 10, and exhibits a small segment, referred to as an advance wire 22, which extends beyond the distal end 20 of the dilatation balloon 12. Advantageously, the advance wire 22 may be of any suitable length, and may be preformed to any desired configuration to facilitate insertion of the catheter 10 and passage through the body lumen.

The proximal end 18 of the dilatation balloon 12 tapers to a diameter which approaches that of the wire 16 to form the shaft 14 of the catheter 10. Thus, the catheter shaft 14 is an extension of the dilatation balloon 12. The catheter shaft 14 provides a path for conducting pressurized fluids into and out of the balloon 12 for selective expansion and deflation thereof. Preferably, the balloon 12 and shaft 14 of the catheter 10 are made of a non-distensible material so that it can only be inflated to expand to the constructed size. Further attempts to inflate such structures result in an increase in pressure, but no significant increase in diameter.

A second wire 24 is movably secured to the catheter shaft 14. As illustrated in FIGS. 1 and 3, the second wire 24 may be external to the catheter shaft 14 and held in place by a thin membrane (not shown). The membrane can cover the entire second wire, or can be disposed at intervals along the length thereof. If the second wire 24 is external to the catheter shaft 14, as illustrated in FIGS. 1-3, the dilatation balloon 12 may exhibit a groove 26 on an outer surface thereof, closed off by a thin membrane 28. The membrane covered groove 26 provides a path through which the second wire 24 may slide. Alternatively, the second wire 24 may be movably retained within the catheter shaft 14 in side by side fashion with the first wire 16, as illustrated in FIG. 3a, or within the catheter shaft 14 but separated from the first wire 16 by a partition 30, as illustrated in FIG. 3b. Preferably, the second wire 24 trails the proximal shoulder 18 of the balloon 12 during insertion of the dilatation catheter 10.

The dilatation catheter 10 illustrated in FIGS. 1-3b is particularly suited for use in distal arteries or severe stenosis. In use, the catheter 10 is inserted into the body lumen until the dilatation balloon 12 is proximate the stenotic area. Preferably, the second wire 24 remains behind the balloon portion of the catheter during the initial insertion across the stenotic region so as to maintain the smallest diameter possible when crossing the lesion. Following several inflations and deflations, the balloon 12 is withdrawn across the lesion while the second wire 24 is advanced beyond the dilated segment. The second wire 24 is left in place in the body lumen for a short period of time, referred to as the post-dilatation observation period, which is usually on the order of 15 minutes to ensure that the lumen will not collapse. If occlusion occurs with the wire 24 still in place across the lesion, then there is access to the distal artery, and the same balloon catheter 10, or a different balloon catheter (not shown), can easily be passed across the lesion and the vessel redilated. Thus, once the wire 24 is in place, the surgeon may pass a larger or smaller balloon catheter over the wire to redilate the body lumen. Likewise, this invention offers the surgeon the option of withdrawing the original balloon catheter and directing over the guide wire 24 a catheter having a different balloon configuration or other medical appliance without the difficulty and time required to once again insert the catheter through the body lumen. In this way, if the result is unsatisfactory, or if dissection or other filling defects obscure the lesion, a balloon catheter can be quickly and safely passed across the lesion over the second wire 24 which has been left in place. This is particularly significant in dealing with the more distal arteries, to which access is often times difficult, in that reinsertion of a fresh catheter may not only prove difficult, but also damaging to the endothelial layer and, in emergency situations, too time consuming, dictating the need for emergency bypass surgery, rather than a second attempt at dilatation.

Figure 12:
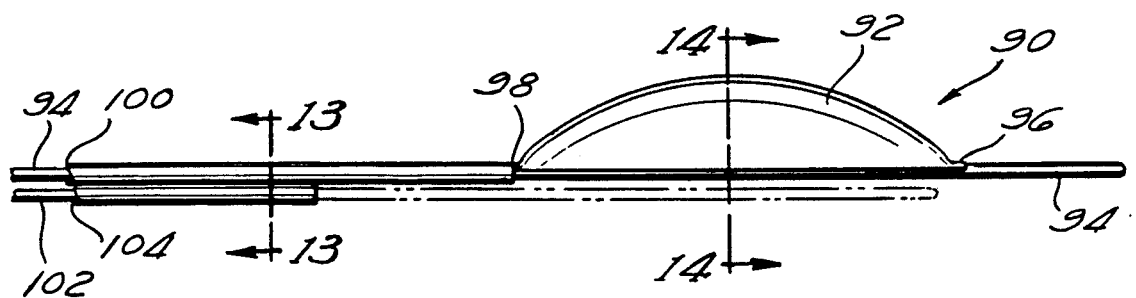
FIG. 12 is a perspective view of a dilatation catheter having a one-sided dilatation balloon, secured to a catheter wire.
Figure 13:
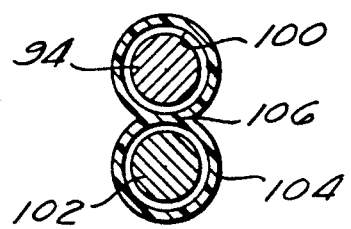
FIG. 13 is a cross-sectional view, taken along line 13—13 of FIG. 12, illustrating the attachment of the one-sided balloon to the catheter wire and the provision of a second, movable wire.
Figure 14:
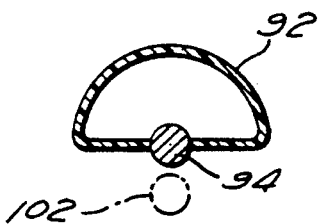
FIG. 14 is a cross-sectional view, taken along line 14—14 of FIG. 12, illustrating the attachment of the dilatation balloon to the catheter wire and, in dotted lines, the positioning of the second wire with respect to the dilatation catheter when advanced.

FIGS. 12-14 illustrate yet an even lower profile dilatation catheter 90. As illustrated, the dilatation balloon 92 of the catheter 90 is a one-sided balloon. The one-sided, or half-circle configuration of the dilatation balloon 92 yields a smaller distal diameter than a balloon which completely encircles the wire 94. Like the catheter 10 illustrated in FIGS. 1-3, the distal end 96 of the one-sided dilatation balloon 92 is secured to directly to the wire 94. The proximal end 98 of the balloon 92 tapers and extends longitudinally along the length of the wire 94 to form an inflation lumen 100. A second, movable wire 102 is retained proximate the catheter 90 by a thin hollow membrane 104, secured to the wire 94 which terminates proximate to the proximal end 98 of the dilatation balloon 92. This catheter 90 is particularly useful in dilating severe stenotic regions, where the passage through the artery is very small. In such an instance, the low profile catheter 90 is inserted into the stenosis and inflated to widen the passageway. The dilatation balloon 92 is then deflated, and the movable wire 102 advanced beyond the stenosis so that a second, larger dilatation may be inserted over the wire 92 to adequately dilate the vessel.

Figure 13A:
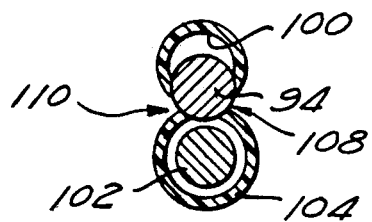
FIG. 13a is a cross-sectional view of an alternative method of securing the second wire to the balloon dilatation catheter of FIG. 12.

As illustrated in FIG. 13, both the hollow membrane 104 and the inflation lumen 100 will form complete circles around the exterior of the movable wire 102 and the catheter wire 94, respectively. The membrane 104 inflation lumen 100 are then secured together so as to share a common outer wall 106. Alternatively, as illustrated in FIG. 13a, the inflation lumen 100 may be wrapped half way around the catheter wire 94 and secured on opposing sides 108, 110 thereof so that the catheter wire 94 forms a portion of the inflation lumen 100. Likewise, the hollow membrane 104 may be wrapped half way around the catheter wire 94 to provide a path through which the movable wire may travel. In the embodiment illustrated in FIG. 13a, the catheter wire 94 provides a common wall for both the inflation lumen 100 and the hollow membrane 104, and thereby yields a smaller diameter catheter shaft.

Figure 6:
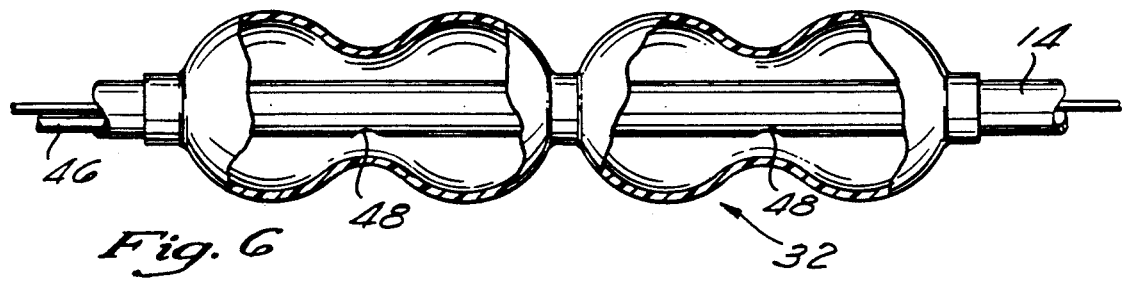
FIG. 6 is a cross-sectional view of a variation of the multi-lobed balloon of FIG. 4, illustrating the combination of two lobes inflated by a single inflation lumen and port.

FIGS. 4-7 are illustrative of a multi-lobed dilatation balloon 32. The multi-lobed balloon 32 is useful in negotiating tortuous vessels and is particularly useful when dilating arteries having acute bends. Preferably, the multi-lobed balloon 32 is a continuous balloon having alternating regions of thick 34 and thin 36 balloon material. The thick portions 34 do not expand as readily as the thin portions 36, and thus the dilatation balloon 32 exhibits multiple lobes, having areas corresponding to the thin portions 36 which readily expand to dilate stenotic areas, and areas corresponding to the thick portions 34 which are resistant to expansion, so as not to straighten arterial bends while the lumen is being dilated. The catheter shaft 14 may be straight, as shown in FIGS. 5 and 6, or it may be preformed with different shapes and configurations to facilitate insertion through the body lumen.

Alternatively, the multi-lobed dilatation balloon 32 may be comprised of a plurality of balloons 38, having overlapping shoulders 40, secured to the exterior of the catheter shaft 14. In such a case, each lobe 38 is advantageously provided with a separate inflation port 42, as illustrated in FIG. 5. As illustrated in FIG. 5, each inflation port may be connected to a separate inflation lumen 44, so that each lobe 38 of the multi-lobed balloon 32 may be separately inflated. Conversely, as illustrated in FIG. 6, a single inflation lumen 46 having a plurality of inflation ports 48 disposed proximate to a lobe of the multi-lobed balloon, or a combination of lobes, may be utilized to inflate each of the lobes simultaneously.

Figure 7:
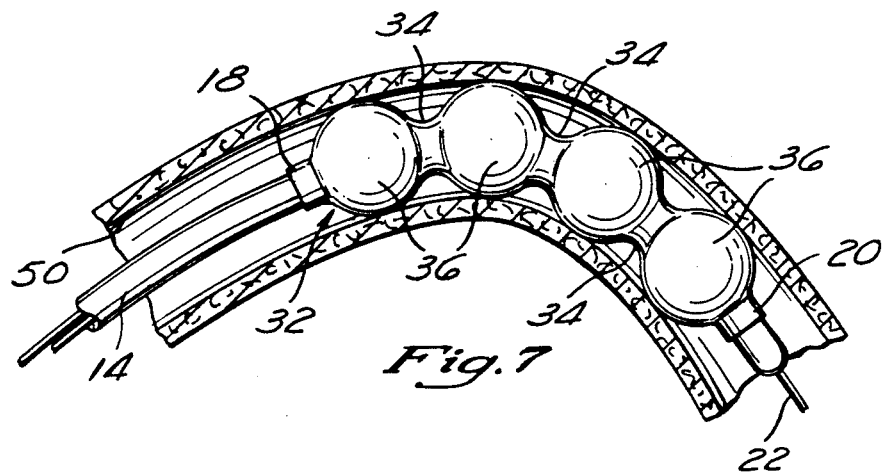
FIG. 7 is a partial cross-sectional view illustrating the dilatation balloon of FIG. 4 positioned within a patient's artery with the lobes inflated.

FIG. 7 illustrates a multi-lobed dilatation balloon 32 in an inflated state, within a bending body lumen 50. Significantly, as illustrated, the multi-lobed balloon 32 does not force the artery 50 to straighten as the balloon is inflated, but rather, conforms to the arterial bends, so as to reduce the risk of dissection of the artery. Further, the multi-lobed construction of the balloon 32 significantly increases the ease of insertion through tortuous vessels over a straight, single lobed balloon, in that the multi-lobed balloon is more flexible.

Figure 8:
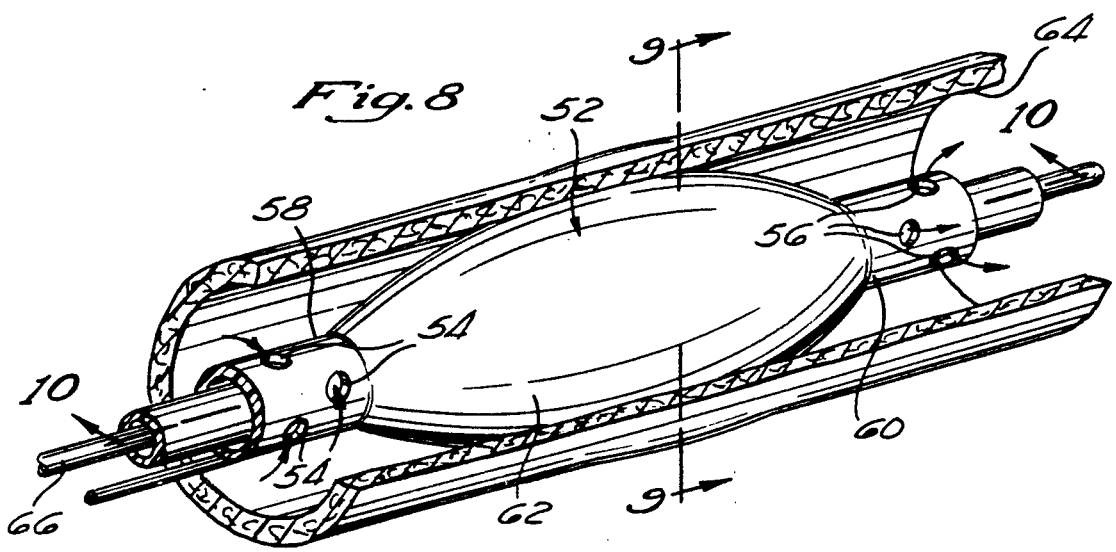
FIG. 8 is a partial cross-sectional view of a dilatation catheter within a patient's artery, having a plurality of perfusion ports for allowing the continuous passage of blood flow through the artery while the balloon is inflated.
Figure 9:
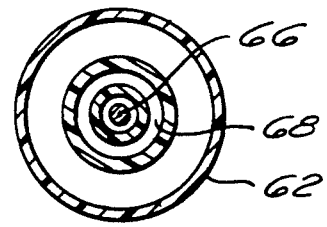
FIG. 9 is a cross-sectional view, taken along line 9—9 of FIG. 8, illustrating the several lumen within the catheter.
Figure 10:
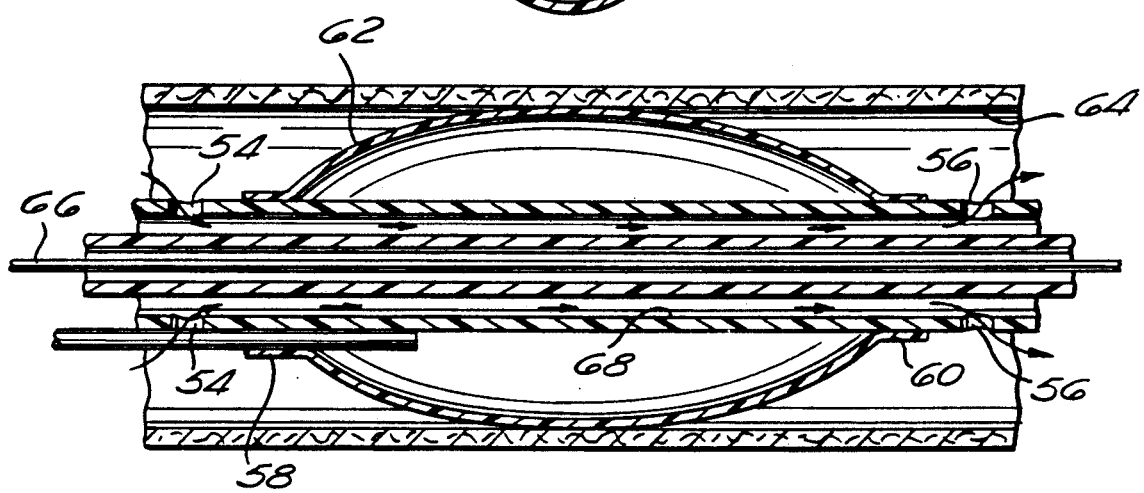
FIG. 10 is a cross-sectional view, taken along line 10—10 of FIG. 8, illustrating, by way of arrows, the perfusion of blood through the inner lumen of the catheter.

FIGS. 8-10 are illustrative of a dilatation balloon catheter 52 having a plurality of perfusion ports 54, 56 on opposite ends 58, 60 of a dilatation balloon 62. As illustrated in FIG. 8, when the balloon 62 is in an inflated state within the artery 64, it completely occludes blood flow past the arterial wall. A bypass lumen 68 which is independent from the lumen through which the guide wire 66 passes, allows blood to perfuse through and bypass the dilation balloon so as to maintain blood flow to the distal side of the occluding balloon. Note that the guide wire need not be withdrawn in order to provide the passage of this blood flow. This is significant in that withdrawal and reinsertion of the guide wire 66 can sometimes result in damage to the arterial walls. Thus, by providing a bypass lumen 68, the dilatation catheter 52 is made safer for the patient.

Not infrequently, it is determined that angioplasty will be unable to restore the blood flow rate to an acceptable level. In such a case, the patient is prepared for emergency bypass surgery. If the catheter is fully withdrawn from the affected vessel and the vessel becomes totally obstructed, infarction of the area distal to the obstruction will begin to occur. A guide wire left in place across the lesion, will provide a small opening through which a small amount of blood may flow beyond the stenosis, however, this blood flow is not usually sufficient to prevent infarction. Advantageously, however, if the dilatation balloon 52 is left across the stenosis in a deflated state, blood will perfuse through the perfusion ports 54, 56 and the bypass lumen 68 to maintain a steady flow of blood distal to the obstruction. Thus, the catheter 52 can effectively serve as a shunt while preparing the patient for emergency bypass surgery.

Figure 11:
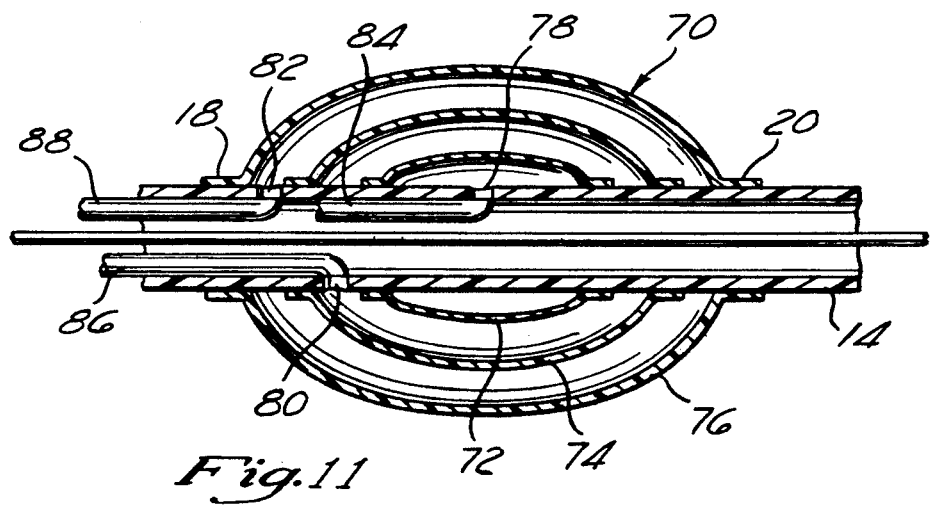
FIG. 11 is a cross sectional view of a multi-layered dilatation balloon in an inflated state.

In many instances, the body lumen, such as the arteries, veins, and other vessels, tubes, and heart valves are hard, or have calcified fibrous lesions which are resistant to dilatation. Standard angioplasty balloons are often not strong enough to dilate the hardened lesions, and are prone to bursting within the artery, necessitating the withdrawal of the catheter and insertion of a new one. Thus, as illustrated in FIG. 11, a dilatation balloon 70, having a plurality of concentric balloon layers 72, 74, 76 is provided. Each balloon layer 72, 74, 76 is provided with a separate inflation port 78, 80, 82 and inflation lumen 84, 86, 88 for selectively inflating the balloon 70. In use, the innermost balloon 72 is inflated first to partially dilate the body lumen. The outer layers 74, 76 of the balloon 70 give additional strength and support to the inner balloon 72 to prevent the inner balloon 72 from bursting. The outer balloons 74, 76 are progressively inflated so as to compress the stenosis radially outwardly, against the adjacent arterial wall. Significantly, the multi-layered balloon 70 of FIG. 11 is also useful in those instances where progressively larger balloons must be used in order to properly dilate the artery or other body lumen or wall of the heart valve.

It will be appreciated that certain structural variations may suggest themselves to those skilled in the art. The foregoing detailed description is to be clearly understood as given by way of illustration, the spirit and scope of this invention being limited solely by the appended claims.

What is claimed is:

1. A dilation catheter for negotiating and dilating tortuous vessels within the body, comprising:
    an axially elongate catheter shaft, suitable for insertion into a body lumen; and
    a multi-lobed dilatation balloon, secured to said catheter shaft, said multi-lobed dilatation balloon being comprised of alternating regions of thick and thin balloon material, wherein said thin portions readily expandable when connected to a source of pressurized fluid so as to radially expand said body lumen, and wherein said thick portions are resistant to expansion, so as to more readily conform to the contours of the body lumen.

* * * * *